United States Patent [19]

Sieja

[11] Patent Number: 4,508,660

[45] Date of Patent: Apr. 2, 1985

[54] CARBONYLATION OF OLEFINICALLY UNSATURATED NITRILES AND ACIDS USING A SULFONE SOLVENT

[75] Inventor: James B. Sieja, Wilmington, Del.

[73] Assignee: E. I. Du Pont de Nemours and Company, Wilmington, Del.

[21] Appl. No.: 475,029

[22] Filed: Mar. 14, 1983

[51] Int. Cl.³ .............. C07C 121/407; C07C 67/38; C07C 51/14
[52] U.S. Cl. ................. 260/465.4; 560/204; 560/233; 562/517; 562/522
[58] Field of Search ............ 260/465.4; 560/233, 560/204; 562/522, 517

[56] References Cited

U.S. PATENT DOCUMENTS

| | | | |
|---|---|---|---|
| 3,346,625 | 10/1967 | Fenton et al. | 260/497 |
| 3,505,394 | 4/1970 | Olivier | 260/497 |
| 3,686,299 | 8/1972 | Carraro et al. | 260/537 |
| 4,032,555 | 6/1977 | Bottaccio et al. | 260/465 |
| 4,224,237 | 9/1980 | Kaplan | 260/449 |
| 4,238,357 | 12/1980 | Pesa et al. | 252/431 |
| 4,313,893 | 2/1982 | Pesa et al. | 260/465.4 |
| 4,344,866 | 8/1982 | Pesa et al. | 252/428 |

FOREIGN PATENT DOCUMENTS

48046  3/1982  European Pat. Off. .

*Primary Examiner*—Joseph Paul Brust

[57] ABSTRACT

Process using selected sulfones, e.g., tetramethylenesulfone as solvents in the carbonylation of nitriles, e.g., 3-pentenenitrile and acids, e.g., 3-pentenoic acid to produce highly linear products.

11 Claims, No Drawings

CARBONYLATION OF OLEFINICALLY UNSATURATED NITRILES AND ACIDS USING A SULFONE SOLVENT

BACKGROUND OF THE INVENTION

1. Field of the Invention

The present invention relates to a process for carbonylating olefinically unsaturated nitriles, e.g., 3-pentenenitrile and acids, e.g., 3-pentenoic acid using certain sulfone solvents, e.g., tetramethylene sulfone to produce highly linear products.

2. Description of the Prior Art

According to U.S. Pat. No. 4,224,237 issued on Sept. 23, 1980, losses of rhodium catalyst are significantly reduced when the reaction of hydrogen and oxides of carbon are conducted within the presence of an organic sulfone solvent. European patent application No. 0,048,046 published on Mar. 24, 1982 teaches that ethylidene diacetate can be produced with good selectivity by reacting methyl acetate and/or dimethyl ether with carbon monoxide and hydrogen in the presence of a catalyst comprising a group VIII metal compound and a bromine- or chlorine-containing compound as a promoter. The reaction is conducted in the substantial absence of water but in the presence of a sulfur-containing polar solvents, e.g., sulfones, sulfoxides and cyclic sulfones.

Carboxylation of organic substrates such as acetophenone and acetone using alkaline phenolates as catalysts is taught in U.S. Pat. No. 4,032,555 issued on June 28, 1977 to be enhanced by the employment of certain oxygenated solvents such as cyclic ethers, e.g., tetrahydrofurane, aliphatic tertiary amines, e.g., triethylamine, heterocyclic tertiary amines, e.g., picoline and cyclic sulfones, e.g., sulpholane.

U.S. Pat. No. 3,505,394 issued on Apr. 17, 1970 discloses oxidative carbonylation in a reaction medium comprising numerous liquid organic solvents including sulfones. The use of a variety of solvents including sulfones in the reaction of butadiene with carbon dioxide in the presence of an amalgam of alkali or alkaline earth metals is disclosed in U.S. Pat. No. 3,686,299 issued Aug. 22, 1972. U.S. Pat. Nos. 4,238,357 issued on Dec. 9, 1980, 4,313,893 issued on Feb. 2, 1982 and 4,344,866 issued on Aug. 17, 1982 disclose a process having improved yields and selectivities of oxygenated organic compounds obtained by contacting an olefinically unsaturated compound with carbon monoxide and a compound containing a replaceable hydrogen atom over a catalyst comprising cobalt and/or ruthenium carbonyl and a promoter ligand consisting of heterocyclic nitrogen compounds and phosphorus or sulfur oxides. Sulfones are among the numerous ligands disclosed. It is believed that these promoter ligands do not function as solvents as evidenced by the fact that the use of solvents not including the sulfur-containing compounds is discussed elsewhere in the specification. Further support for this conclusion is that the rate of reaction is taught to substantially decrease as the ratio of ligand to cobalt and/or ruthenium carbonyl increases.

U.S. Pat. No. 3,346,625 issued on Oct. 10, 1967 discloses a process for the oxidative carbonylation of olefins using a platinum catalyst and, optionally, a redox reagent and an inorganic dehydrating agent such as a molecular sieve. The Patentees teach that the reaction can be conducted in a liquid phase organic solvent and include within their operable solvents ketone, amides, sulfones, ethers, esters, lower molecular weight fatty acids or benzene carboxylic acids. No particular advantage is assigned to the use of sulfone solvents.

SUMMARY OF THE INVENTION

The present invention is a process for carbonylating compounds of the formula $R_1A$ wherein $R_1$ is selected from a group consisting of alkenyl groups having 3-6 carbon atoms and substituted alkenyl groups having 4-8 carbon atoms and A is selected from the groups consisting of $C\equiv N$ and

e.g., 3-pentenenitrile and 3-pentenoic acid and mixtures thereof comprising reacting said compounds with carbon monoxide and a compound having the formula $R_2OH$ wherein $R_2$ is a group selected from the groups H and alkyl and substituted alkyl groups having 1–12 carbon atoms, e.g., water and methanol in the presence of a sulfone solvent having the formula

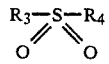

wherein $R_3$ and $R_4$ are the same or different and are optionally cojoined and are groups selected from alkyl groups having 1–4 carbon atoms and substituted alkyl groups having 4–8 carbon atoms and when $R_3$ and $R_4$ are cojoined aliphatic alkylene groups and substituted alkylene groups having 2–4 carbon atoms. A carbonylation catalyst such as cobalt carbonyl is employed. The mole ratio of the sulfone, preferably tetramethylene sulfone, to the compound $R_1A$ is in the range of 1/1–5/1 and preferably 2.5/1–4/1.

DETAILED DESCRIPTION OF THE INVENTION

The starting materials to which the present invention is applied include certain olefinic nitriles and acids. The nitrile starting materials are defined by the formula $R_1CN$ wherein $R_1$ is an alkenyl group having 3–6 carbon atoms and substituted alkenyl groups having 4–8 carbon atoms, e.g., 3-butenenitrile, 2-butenenitrile, 3-, 4-heptenenitrile, 2-pentenenitrile, 3-pentenenitrile and 4-pentenenitrile, methacrylonitrile, 3-propyl-3-pentenenitrile, 2-butyl-2-butenenitrile, 3,4-dimethyl-hexenenitrile. The preferred nitriles are the unsubstituted pentenenitriles, e.g., 2-, 3-, and 4-pentenenitrile.

The olefinic acid starting materials are defined by the formula

where $R_1$ is an alkenyl group having 3–6 carbon atoms and substituted alkenyl groups having 4–8 carbon atoms including e.g., 2-pentenoic acid, 2-methyl-2-pentenoic acid, 3-hexenoic acid, 3-heptenoic acid, 2,3-dimethyl-2-pentenoic acid, 3-butenoic acid, 2-butenoic acid, 3- pentenoic acid, 3-propyl-3-pentenoic acid, 2-butyl-2-butenoic acid, 3,4-dimethylhexenoic acid.

The replaceable hydrogen atoms in the carbonylation are supplied by water or an alcohol defined by the formula $$R_2OH$$

wherein $R_2$ is an alkyl or substituted alkyl group having 1–12 and preferably 1–4 carbon atoms. Illustrative of operable alcohols are methanol, ethanol, butanol, n-pentyl alcohol, isoamyl alcohol, octanol, isopropanol, propanol, isobutanol, and dodecanol. Water and methanol are the preferred sources of replaceable hydrogen atoms.

The carbonylation catalysts which in combination with the sulfone solvents provide exceptionally linear products in good yield are cobalt compounds including or selected from the group consisting of cobalt salts of Bronsted acids, carbon monoxide derivatives of cobalt and organometallic cobalt compounds. It is believed that negatively charged cobalt is the active catalyst species and that it can be formed in situ from a variety of compounds such as those of the general types discussed above. Suitable salts are cobaltous and cobaltic chloride, iodide, bromide, propionate, butyrate, isobutyrate, acetate, carbonate, benzoate, valerate, 5-cyanovalerate, pentenoate, and hydroxide. Suitable organometallic cobalt compounds include cobalt acetylacetonate, dicyclopentadienyl cobalt, π-allyl cobalttricarbonyl, and π-crotyl cobalttricarbonyl. Compounds which are carbon monoxide derivatives of cobalt include dicobalt octacarbonyl, cobalt nitrosyltricarbonyl, cyclopentadienylcobalt dicarbonyl and tetracobalt-dodecacarbonyl.

The sulfone solvents which in combination with the catalyst and starting materials provide the superior results of the present invention are defined by the formula $$R_3-S-R_4$$
$$\underset{O}{\overset{O}{\diagup\diagdown}}$$

wherein $R_3$ and $R_4$ are the same or different and are optionally cojoined and are selected from alkyl groups having 1–4 carbon atoms and substituted alkyl groups having 4–8 carbon atoms and when $R_3$ and $R_4$ are cojoined aliphatic alkylene and substituted alkylene groups having 2–4 carbon atoms. Illustrative of the above sulfones are methylethylsulfone, diisobutylsulfone, n-butyl isobutyl sulfone, octamethylenesulfone, pentamethylenesulfone and 3-methylpentamethylenesulfone. Diethylsulfone, dibutylsulfone and dipropylsulfone are the preferred sulfones. Dimethylsulfone, tetramethylenesulfone and 3-methyltetramethylenesulfone are especially preferred. Varying amounts of sulfone can be employed in the present invention but generally the mole ratio of sulfone to the starting olefinic nitrile or acid is at least 0.5/1, usually in the range 1/1–5/1 and preferably in the range 2.5/1–4/1.

The source of carbon monoxide is not critical to the present invention. Commercial grade (98%) and ultrahigh purity grade (99.8%) are both satisfactory. The presence of from 0.1–10% $H_2$ in the carbon monoxide has been found to have a beneficial effect on reaction rate.

The relative amounts of olefinic nitrile or acid starting material, carbon monoxide and the compound containing replaceable hydrogen can vary fairly widely but it is preferred that they be maintained in a mole ratio of olefinic nitrile or acid starting material to carbon monoxide to the compound containing replaceable hydrogen of 1/1/1 respectively, and preferably 1/10/1.5.

The process of the present invention can be conducted under a wide range of conditions. Temperatures of up to 250° C. can be employed although it is usual to operate the process at temperatures in the range of 140°–200° C. and preferably 160°–180° C. in order to maintain the reactants in a substantially liquid condition. The pressure under which the present process is conducted can also be varied over a wide range. Low pressures, e.g., 6.9 MPa can be employed but it is preferred to employ pressures in the range of 15–41 MPa and most preferably in the range 21–31 MPa. Higher pressures, e.g., 52 MPa may be employed but do not contribute significantly to the overall performance and/or yield of the present process while increasing the investment and energy cost involved. Thus, there is little incentive to conduct the process at pressures higher than the preferred pressures.

In the continuous practice of the process of the present invention the sulfone solvent, nitrile or acid, the compound containing replaceable hydrogen, the cobalt catalyst and carbon monoxide are introduced into a reactor and maintained at reaction temperature and pressure for the desired time following which the reaction product is flash cooled by reducing its pressure to ambient. The vapor stream which contains alcohol, water and unreacted starting material can be recycled to the reactor after treatment to remove volatile impurities. The liquid portion of the flashed product is contacted with a solvent to extract the desired product and thereby separate it from the catalyst, solvent and by-products. The extracted product is then purified by means obvious to those skilled in the art. In a specific example, approximately 27 parts of 2-pentenenitrile, 15 parts methanol, 4.4 parts dicobalt octacarbonyl and 175 parts of dimethyl sulfone are introduced into a reactor and maintained at 180° C. and 31 MPa pressure with carbon monoxide. After holdup for about 5 hours, the reaction product is cooled by flash evaporation. Methanol, unreacted 2-pentenenitrile and any valeronitrile produced is taken overhead. Approximately 200 parts of the resultant product containing the sulfone solvent, methyl 5-cyanovalerate and methyl 2-methyl-4-cyanobutyrate, and catalyst is contacted with 200 parts of a solvent to extract the methyl 5-cyanovalerate. After contact with the solvent, the unextracted sulfone and catalyst are recycled to the reactor. The solvent is then separated from the methyl 5-cyanovalerate and recycled to the solvent extraction step. The methyl 5-cyanovalerate is purified according to known procedures. Suitable variations of the above described process should be apparent to those skilled in the art.

The following examples are presented to illustrate but not to restrict the present invention. Parts and percentages are by weight unless otherwise noted.

EXAMPLE 1

Approximately 4.4 parts of dicobalt octacarbonyl, 26.4 parts cis-2-pentenenitrile, 142 parts of tetramethylene sulfone, and 20 parts of methanol were charged to a magnetically stirred stainless steel autoclave. After the charge was complete the autoclave was sealed and heated with stirring to 180° C. under 31 MPa carbon monoxide pressure. After approximately 4 hours at these conditions, the autoclave was cooled to ambient temperature and the contents analyzed. It was found that the conversion of pentenenitrile was 92% and the yield of methyl 5-cyanovalerate was 92%. The following compounds were also formed at the yields indicated; valeronitrile 5.5%, dimethyl ethyl succinate 0.08%, methyl 2-cyanovalerate 0.24%, methyl 2-ethyl-3-cyanopropionate 0.085%, methyl 2-methyl-4-cyanobutyrate 4.8% and methyl acetate 0.5 moles per mole of valeronitrile.

EXAMPLE 2

Approximately 4 parts of dicobaltoctacarbonyl, 21 parts of 3-pentenenitrile, 150 parts of tetramethylenesulfone, and 20 parts of methanol were charged to a magnetically stirred stainless steel autoclave. After the charge was complete, the autoclave was sealed, heated with stirring to 160° C. and pressurized to 21 MPa with carbon monoxide. After approximately four hours at these conditions, the autoclave was cooled to ambient temperature and the contents analyzed. It was found that the conversion of pentenenitrile was 55%, and the yield of methyl 5-cyanovalerate was 93%. The following compounds were also found in the yields indicated: valeronitrile 2.5%, methyl 2-cyanovalerate 0.5%, methyl 2-methyl-4-cyanobutyrate 3.5%.

EXAMPLE 3

Approximately 4 parts of dicobaltoctacarbonyl, 20 parts of 2-pentenenitrile, A 150 parts of tetramethylenesulfone, and 20 parts of methanol were charged to a magnetically stirred stainless steel autoclave. After the charge was complete, the autoclave was sealed, heated with stirring to 160° C. and pressurized to 21 MPa with carbon monoxide. After approximately four hours at these conditions, the autoclave was cooled to ambient temperature and the contents analyzed. It was found that the conversion of pentenenitrile was 78%, and the yield of methyl 5-cyanovalerate was 93%. The following compounds were also found in the yields indicated: valeronitrile 3%, methyl 2-methyl-4-cyanobutyrate 3%.

EXAMPLE 4

A 10 ml stainless steel pressure tube was charged with 6.2 g of dimethylsulfone, 0.6 g 2-pentenoic acid, 0.04 g dicobaltoctacarbonyl, and 0.25 ml water. The contents of the tube were held at 160° C. under carbon monoxide pressure for four hours. Analysis of the contents indicated that about 64% of the 2-pentenoic acid was converted to a mixture of diacids in the following relative weights: ethylsuccinic acid, methylglutaric acid, adipic acid, 1/1/3.6.

EXAMPLE 5

A 10 ml stainless steel pressure tube was charged with 4 ml of 3-methylsulfone, 1 ml of 3-pentenenitrile, 1 ml of methanol, and 0.1 g of dicobaltoctacarbonyl. The contents of the tube were held at 160° C. under 21 MPa carbon monoxide pressure for four hours. Analysis of the contents indicated the following compounds to be formed in the relative weights: methyl 2-cyanovalerate, methyl 2-ethyl-3-cyanopropionate, methyl 2-methyl-4-cyanobutyrate, methyl 5-cyanovalerate, 1.4/0.2/5.5/93.

I claim:

1. A process for cabonylating compounds of the formula $R_1A$ wherein $R_1$ is selected from a group consisting of alkenyl groups having 3-8 carbon atoms and A is selected from the groups consisting of $C\equiv N$ and

and mixtures thereof comprising reacting said compounds at a temperature up to 250° C. with carbon monoxide and a compound having the formula $R_2OH$ wherein $R_2$ is selected from the groups H and alkyl groups having 1-12 carbon atoms in the pressure of a sulfone solvent having the formula

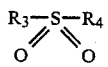

wherein $R_3$ and $R_4$ are the same or different and are optionally cojoined and are selected from alkyl groups having 1-8 carbon atoms and when $R_3$ and $R_4$ are cojoined aliphatic alkylene groups having 2-4 carbon atoms wherein solvent amounts of a mole ratio of the sulfone to the starting $R_1A$ compound of at least 0.5/1 is employed and said process being carried out in the presence of a cobalt containing carbonylation catalyst.

2. The process of claim 1 wherein the mole ratio of the sulfone to the compound $R_1A$ is in the range 1/1-5/1.

3. The process of claim 1 wherein $R_3$ and $R_4$ are methyl groups.

4. The process of claim 1 wherein $R_2$ is a group having 1-4 carbon atoms and $R_3$ and $R_4$ are cojoined and are ethylene groups and substituted ethylene groups having 3-4 carbon atoms.

5. The process of claim 2 wherein the sulfone is tetramethylene sulfone.

6. The process of claim 4 wherein the mole ratio of the sulfone to the compound $R_1A$ is in the range 2.5/1-5/1.

7. The process of claim 2 wherein the carbonylation catalyst is a cobalt salt.

8. The process of claim 2 wherein the carbonylation catalyst is cobalt carbonyl.

9. A process for the carbonylation of compounds selected from the group consisting of pentenoic acids and pentenenitriles to essentially linear products comprising contacting said nitrile with carbon monoxide and water at a temperature in the range 140°-200° C. and a pressure in the range 14-35 MPa in the presence of a tetraalkylene sulfone as a solvent wherein the mole ratio of the sulfone to the acid or nitrile reactant is at at least 0.5/1 and in the presence of a cobalt salt as a carbonylation catalyst.

10. The process of claim 9 wherein the cobalt salt is cobalt carbonyl.

11. In a process for the carbonylation of pentene nitriles and pentenoic acids in the presence of cobalt containing catalysts to linear products, the improvement which comprises conducting the carbonylation in the presence of a sulfone solvent having the formula

wherein $R_3$ and $R_4$ are the same or different and are optionally cojoined and are selected from alkyl groups having 1-8 carbon atoms and when $R_3$ and $R_4$ are cojoined aliphatic alkylene groups having 2-4 carbon atoms at a temperature up to about 250° C. and wherein solvent amounts of a mole ratio of the sulfone to the nitrile or acid reactant of at least 0.5/1 is employed.

* * * * *

UNITED STATES PATENT OFFICE
CERTIFICATE OF CORRECTION

PATENT NO. : 4,508,660
DATED : April 2, 1985
INVENTOR(S) : JAMES B. SIEJA

It is certified that error appears in the above-identified patent and that said Letters Patent are hereby corrected as shown below:

Claim 1, Column 6, line 9, "pressure" should be -- presence --.

Signed and Sealed this

Thirteenth Day of August 1985

[SEAL]

Attest:

DONALD J. QUIGG

Attesting Officer     Acting Commissioner of Patents and Trademarks